Figure 1:
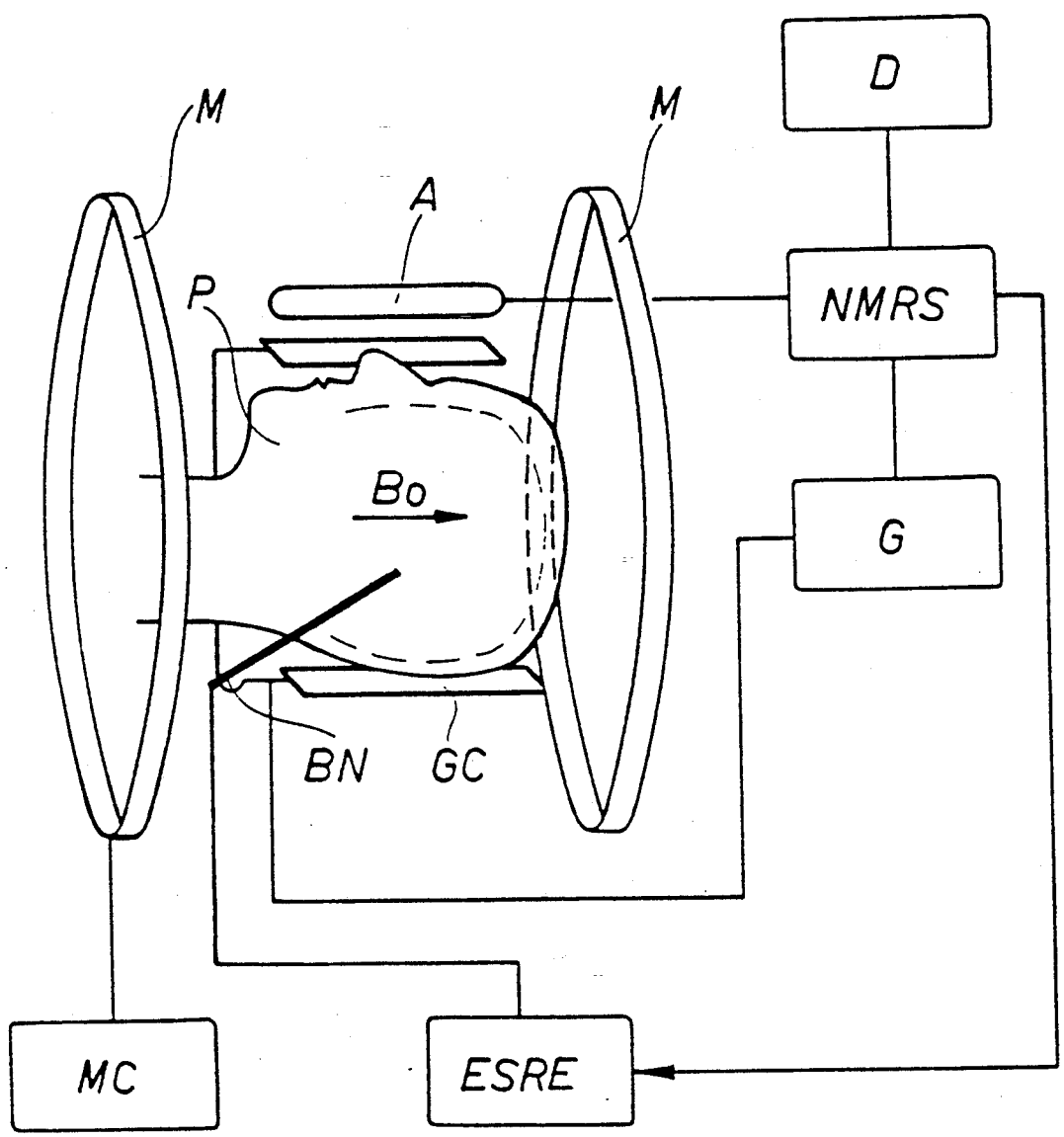

United States Patent [19]

Sepponen

[11] Patent Number: 5,211,166
[45] Date of Patent: May 18, 1993

[54] OPERATIVE INSTRUMENT PROVIDING ENHANCED VISIBILITY AREA IN MR IMAGE

[75] Inventor: Raimo Sepponen, Helsinki, Finland

[73] Assignee: Instrumentarium Corp., Finland

[21] Appl. No.: 773,254

[22] Filed: Oct. 9, 1991

Related U.S. Application Data

[63] Continuation of Ser. No. 428,238, Oct. 27, 1989, abandoned.

[30] Foreign Application Priority Data

Nov. 11, 1988 [FI] Finland .................................. 885210

[51] Int. Cl.$^5$ ............................................ A61B 5/055
[52] U.S. Cl. ................................ 128/653.5; 128/653.2; 324/307
[58] Field of Search ............... 128/653.2, 653.4, 653.5; 324/307

[56] References Cited

U.S. PATENT DOCUMENTS

| | | | |
|---|---|---|---|
| 4,618,978 | 10/1986 | Cosman | 378/164 |
| 4,719,425 | 1/1988 | Ettinger | 324/316 |
| 4,749,560 | 6/1988 | Elgavish | 424/9 |
| 4,827,931 | 5/1989 | Longmore | 128/334 R |
| 4,891,593 | 1/1990 | Lurie et al. | 324/307 |
| 4,989,608 | 2/1991 | Ratner | 128/653 |

OTHER PUBLICATIONS

Lepley, A. R. and Closs, G. L., "Chemically induced magnetic polarization", Wiley, New York, 1973.
Maciel, G. E. and Davis, M. P., "NMR imaging of paramagnetic centers in solids via dynamic nuclear polarization", J. Magn. Reson., vol. 64, pp. 356-360, 1985.
Lurie D. J., Bussel, D. M., Bell, L. H., Mallard, J. R., "Proton Electron Double Resonance Imaging: A new method for imaging free radicals", Proc. (cont'd.) S.M.R.M. Fifth Annual Meeting, 1987, New York, p. 24.
Lurie, D. J., Bussel, D. M., Bell, L. H., Mallard, J. R., "Proton-Electron Double Magnetic Imaging of free radical solutions", J. Magn. Reson., vol. 76, (cont'd.) 1988, pp. 366-370.
Potenza, J., "Measurement and applications of dynamic nuclear polarization", Adv. Mol. Relaxation Processes, 1972.
Röschmann, P., "Radiofrequency penetration and absorption in the human body: Limitations to high-field whole-body nuclear magnetic resonance imaging", Med. Phys. 14, 1987.

*Primary Examiner*—Ruth S. Smith
*Attorney, Agent, or Firm*—Andrus, Sceales, Starke & Sawall

[57] ABSTRACT

An operative instrument for the examination of an object, for example a biopsy tube or a capsule of a radioactive substance intended for radiation therapy. A part of the operative instrument, the active part, is adapted to be detected by NMR methods, such as magnetic resonance imaging, either in a manner that the active part contains a substance having NMR active nuclei or in a manner that the NMR active nuclei in proximity of the active part of the object can emit NMR signals in connection with an NMR or magnetic resonance imaging examination arrangement. A substance, a relaxant, is arranged in interaction with said NMR active nuclei, said relaxant causing activation of the NMR signal by means of dynamic nuclear polarization (DNP) when the electron spin system of said substances is saturated with external energy, i.e. saturation energy.

10 Claims, 5 Drawing Sheets

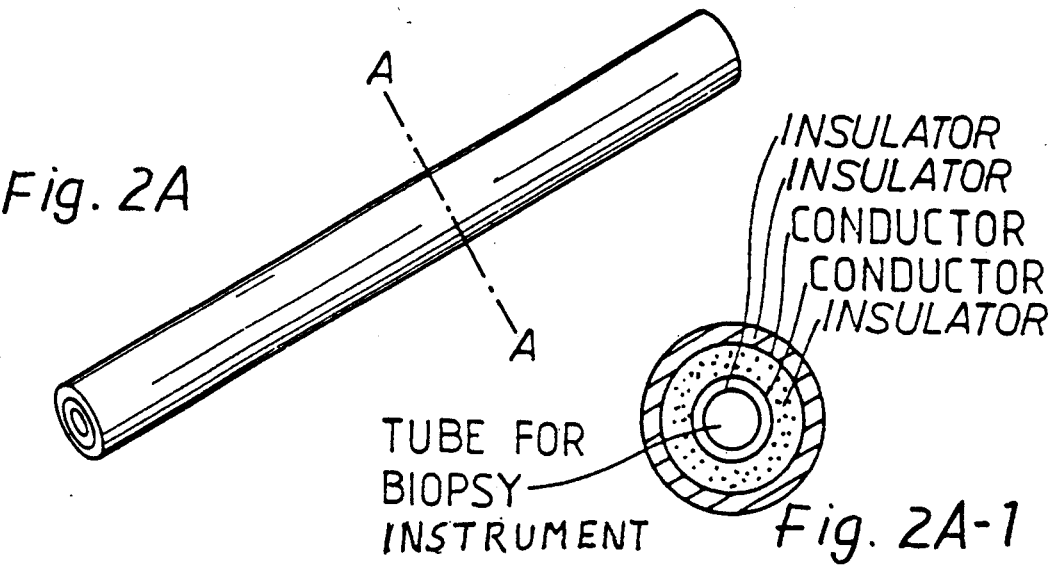
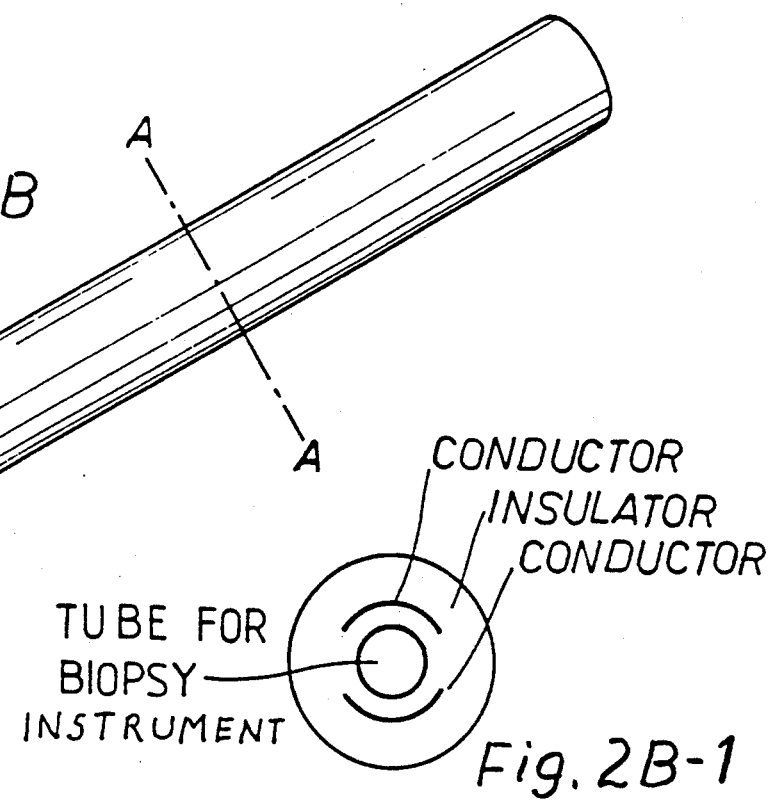

OPERATIVE INSTRUMENT PROVIDING ENHANCED VISIBILITY AREA IN MR IMAGE

The present application is a continuation application of U.S. patent application Ser. No. 07/428,238, filed Oct. 27, 1989, now abandoned.

The present invention relates to an arrangement for the examination of an object, such as a human body, an animal, the trunk of a tree or a foodstuff and possibly for the simultaneous control of treatment procedures.

Magnetic resonance imaging (MRI) is a method that utilizes a nuclear magnetic resonance phenomenon (NMR) for the determination of local distributions of the nuclear density and NMR characteristics relating to the nuclei of an object or the physical and chemical characteristics affecting them. Said NMR characteristics include e.g.: longitudinal relaxation (characterized by longitudinal relaxation time T1), transverse relaxation (characterized by transverse relaxation time T2), relaxation in the rotating frame of reference (characterized by relaxation time T1rho), chemical shift, and coupling factors between nuclei. The NMR characteristics are affected by the physicochemical environment of the nuclei: a polarizing magnetic field $B_o$, flow rate, diffusion, paramagnetic materials, ferromagnetic materials, viscosity and temperature.

The methods and applications of magnetic resonance and magnetic resonance imaging have been studied in a number of references: Poole C. P. and Farach H. A., Theory of magnetic resonance, John Wiley, New York 1987; Stark D. D. and Bradley W. G., Magnetic resonance imaging, C. V. Mosby Comp., St. Louis 1988; Gadian D. G., Nuclear magnetic resonance and its applications to living systems, Oxford Univ. Press, London 1982; Shaw D., Fourier transform NMR spectroscopy, Elsevier, Amsterdam 1984; Battochletti J. H., NMR proton imaging, CRC Crit. Rev. Biomed. Eng. vol. 11, pp. 313–356, 1984; Mansfield P. and Morris P. G., NMR imaging in biomedicine, Adv. in magnetic resonance, Academic Press, New York 1982; Abragam A., The principles of nuclear magnetism, Clarendon Press, Oxford 1961; Fukushima E. and Roeder S. B. W., Experimental Pulse NMR, Addison-Wesley, Readin, Mass. 1981; Lasker S. E. and Milvy P (eds.), Electron spin resonance and nuclear magnetic resonance in biology and medicine and magnetic resonance in biological systems, Annals of New York Academy of Sciences vol. 222, New York Academy of Sciences 1973; Sepponen S. E., Discrimination and characterization of biological tissues with magnetic resonance imaging; A study of methods for T1, T2, T1rho and chemical shift imaging, Acta Polytechnica Scandinavica EL-56, Helsinki 1986; Fukushima E. and Roeder S. B., Experimental pulse NMR, Addison-Wesley, London 1981; Anderson W. A. et al, U.S Pat. No. 3,475,680; Ernst R. R., U.S Pat. No. 3,501,691; Tomlinson B. L. et al, U.S Pat. No. 4,034,191; Ernst R. R., U.S. Pat. No. 3,873,909; Ernst RR, U.S Pat. No. 4,070,611; Bertrand R. D. et al, U.S Pat. No. 4,345,207; Young I. R., U.S. Pat. No. 4,563,647; Hofer D. C. et al, U.S. Pat. No. 4,110,681; Savelainen M. K., Magnetic resonance imaging at 0.02 T: Design and evaluation of radio frequency coils with wave winding, Acta Polytechnica Scandinavica Ph 158, Helsinki 1988; Sepponen R. E., U.S. Pat. No. 4,743, 650; Sepponen R. E., U.S. Pat. No. 4,654,595; Savelainen M. K., U.S. Pat. No. 4,712,068; Sepponen R. E., U.S. Pat. No. 4,587,493; Savelainen M. K., U.S. Pat. No. 4 644 281; and Kupiainen J., U.S. Pat. No. 4,668,904

In addition to the above, dynamic nuclear polarization has been studied e.g. in the following references: Lepley A. R. and Closs G. L., Chemically induced magnetic polarization, Wiley, New York 1973; and Potenza J., Measurement and Applications of dynamic nuclear polarization, Adv. Mol. Relaxation Processes vol. 4, Elsevier, Amsterdam 1972, pp. 229–354.

DNP is a magnetic double resonance method. It thus requires two separate spin populations. Such spin populations include e.g. the spins of electrons and protons. In the double resonance method, the distribution of one spin population at various energy levels is varied and the other spin population is observed. As certain conditions are fulfilled, the resonance signal of a spin population being observed increases (Overhauser phenomenon). The amplified signal can have an amplitude that is several hundred times higher than a non-amplified signal. The amplification factor can be positive or negative. The amplified signal has properties that make it highly sensitive to the physicochemical characteristics and reactions of a spin environment, so its application for the examination of the chemical characteristics of a material is obvious.

The reference Maciel G. E., Davis M. F., NMR imaging of paramagnetic centers in solids via dynamic nuclear polarization, J Magn. Reson., vol. 64, pp. 356–360, 1985 discloses a method suitable for mapping paramagnetic components by combining DNP and MRI methods. The reference Ettinger K. V., U.S. Pat. No. 4,719,425 discloses as its applications the mappings of the contents of paramagnetic components and the activity of cerebral nerve cells. The references Lurie D. J., Bussel D. M., Bell L. H., Mallard J. R., Proton Electron Double Resonance Imaging: A new method for imaging free radicals, Proc. S.M.R.M. Fifth Annual Meeting, 1987, New York, p. 24 and Lurie D. J., Bussel D. M., Bell L. H., Mallard J. R., Proton-Electron Double Magnetic Resonance Imaging of free radical solutions, J. Magn. Reson., vol. 76, 1988, pp. 366–370 discloses as possible applications the mappings of free radical groups, nitroxide radicals and degree of oxidation.

According to the prior art, an electron spin system is saturated by radiating an object at a frequency which corresponds to the electron spin resonance or ESR frequency in field B and detecting an NMR signal at a frequency which corresponds to field strength $B_o$. For example, for the $B_o$ strength of 0.04T the corresponding ESR frequency is 1.12 GHz and the corresponding NMR frequency is 1.7 MHz.

A problem in the prior art is the absorption of NMR frequency electromagnetic oscillations in an object being examined. This leads to two major drawbacks: 1. The saturation occurring at the ESR frequency takes place in only those parts of an object which are close to the emitter (e.g. the penetration depth of 1.12 GHz in muscular tissue is less than 3 cm). 2. Since the width of an ESR line is relatively large, the saturation requires the use of high power which, when absorbed in an object, may cause damage to the object (heating).

The interaction of electromagnetic radiation and a biological tissue has been studied e.g. in the following references: Röschmann P, Radiofrequency penetration and absorption in the human body: Limitations to high field whole body nuclear magnetic resonance imaging, Med. Phys. 14(6), pp. 922–931, 1987; Tenforde T. S. and Budinger T. P., Biological effects and physical safety aspects of NMR imaging and in vivo spectroscopy, in Thomas S. R. and Dixon R. L. (eds.) NMR in medicine: The instrumentation and clinical applications, Medical Physics Monograph No. 14, American Institute of Physics, New York 1986.

Prior known are the catheters disclosed in reference Longmore, U.S. Pat. No. 4,827,931, which are partially or completely manufactured from a material visible in a normal magnetic resonance image. However, the emitted NMR signal of these is relatively weak and requires a long imaging time.

Prior known are methods suitable for so-called high-speed magnetic resonance imaging which are described e.g. in the following references: Rzedzian R. R. et al, Lancet, December 3, p. 1281, 1983; Haase A. et al, J. Magn. Reson., vol. 67, p. 258, 1986; Pykett I. L. et al, Magn. Reson. in Med., vol. 5, p. 563, 1987.

It is also prior known to employ modules that are fixed relative to the anatomy of a patient for creating positional coordinates. Parts of these modules are provided with a material detectable in imaging for creating reference points. Such prior known products include Leksell Stereotactic Instrument, manufactured by Elekta Instrument AB, Stockholm, Sweden and Orfit Raycast thermoplastic which are used e.g. in radiotherapy for positioning a patient, the latter being manufactured by Luxilon Industries & Co., Antwerpen, Belgium. The application of stereotactic methods has been described in the references: Leksell et al, Stereotaxis and nuclear magnetic resonance, J Neurology, Neurosurgery and Psychia; try, vol. 48, pp. 14–18, 1985; Lehmann and Hill, Computed-tomography—directed stereotaxis for movement disorder with postoperative magnetic resonance imaging confirmation, Appl. Neurophysiol., Vol. 51: pp. 21–28, 1988; Kelly et al, Evolution of contemporary instrumentation for computer assisted stereotactic surgery, Surg. Neurol., vol. 30, pp. 204–215, 1988; and Kaneko et al, Treatment of brain tumors with iridium-92 seeds, Acta Oncologica, vol. 27, Fasc 3, 269–274, 1988.

In practice, locating a surgical instrument, a biopsy needle, a radioactive capsule, or other operative instrument, relative to various tissue portions must be effected with an accuracy as precise as possible. Hereinafter, the location of an instrument of interest, within an object at any given moment, will be called the operating location. In imaging, accurate locating requires a good contrast and signal-to-noise ratio between said instrument or a part thereof and the tissue of the operating location.

The present invention provides an operative instrument that meets the foregoing requirements.

Figure 3A:
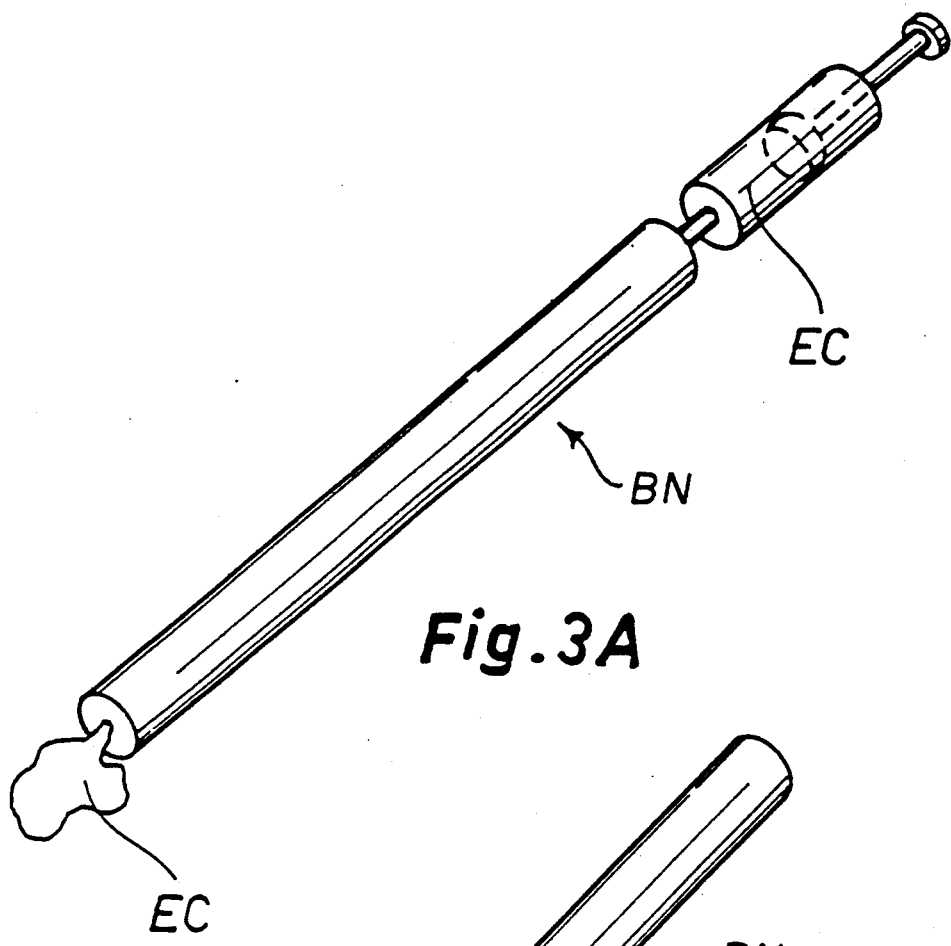
Figure 3B:
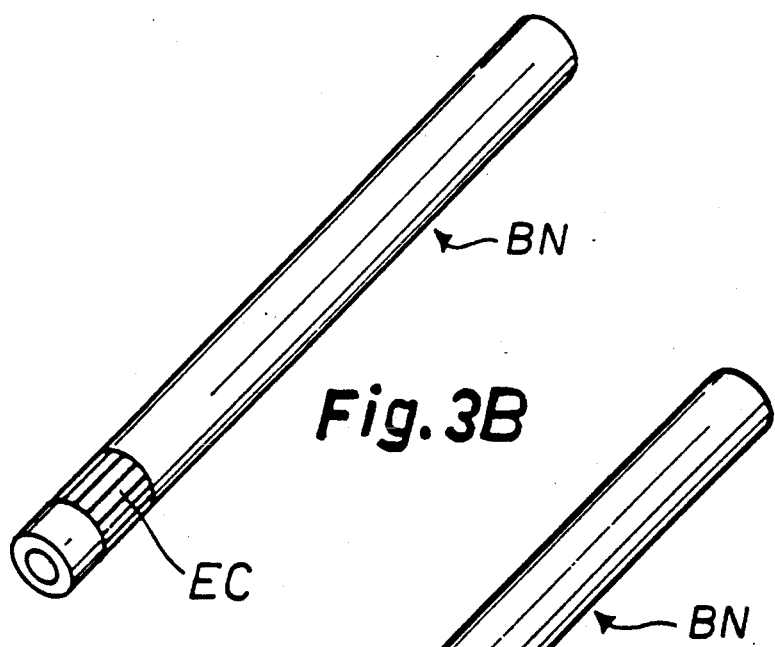
Figure 3C:
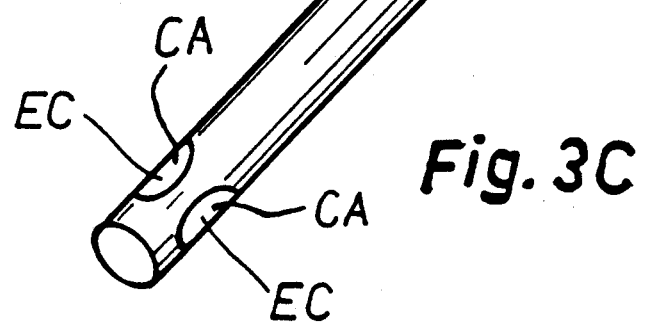
Figure 4:
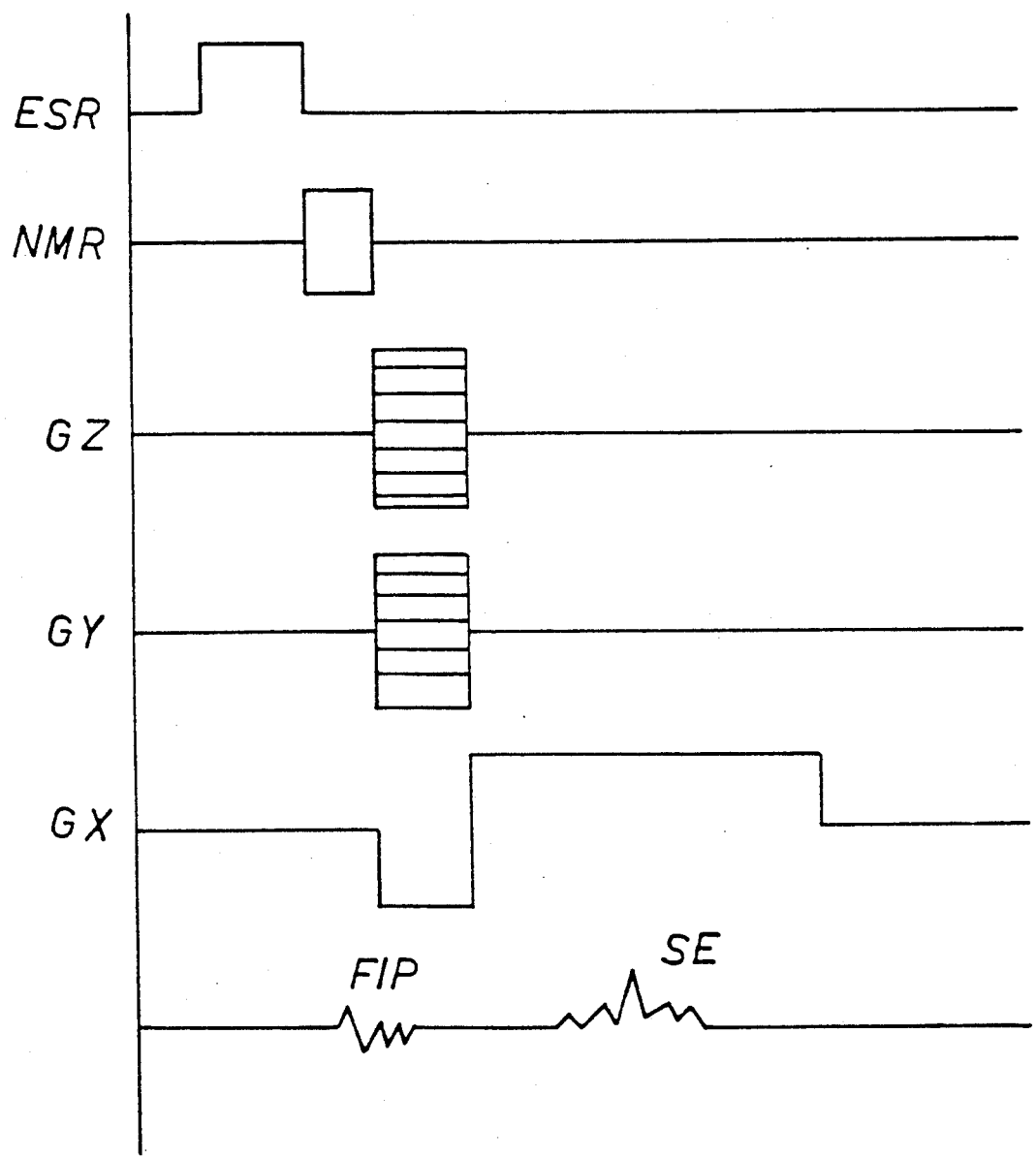
Figure 5:
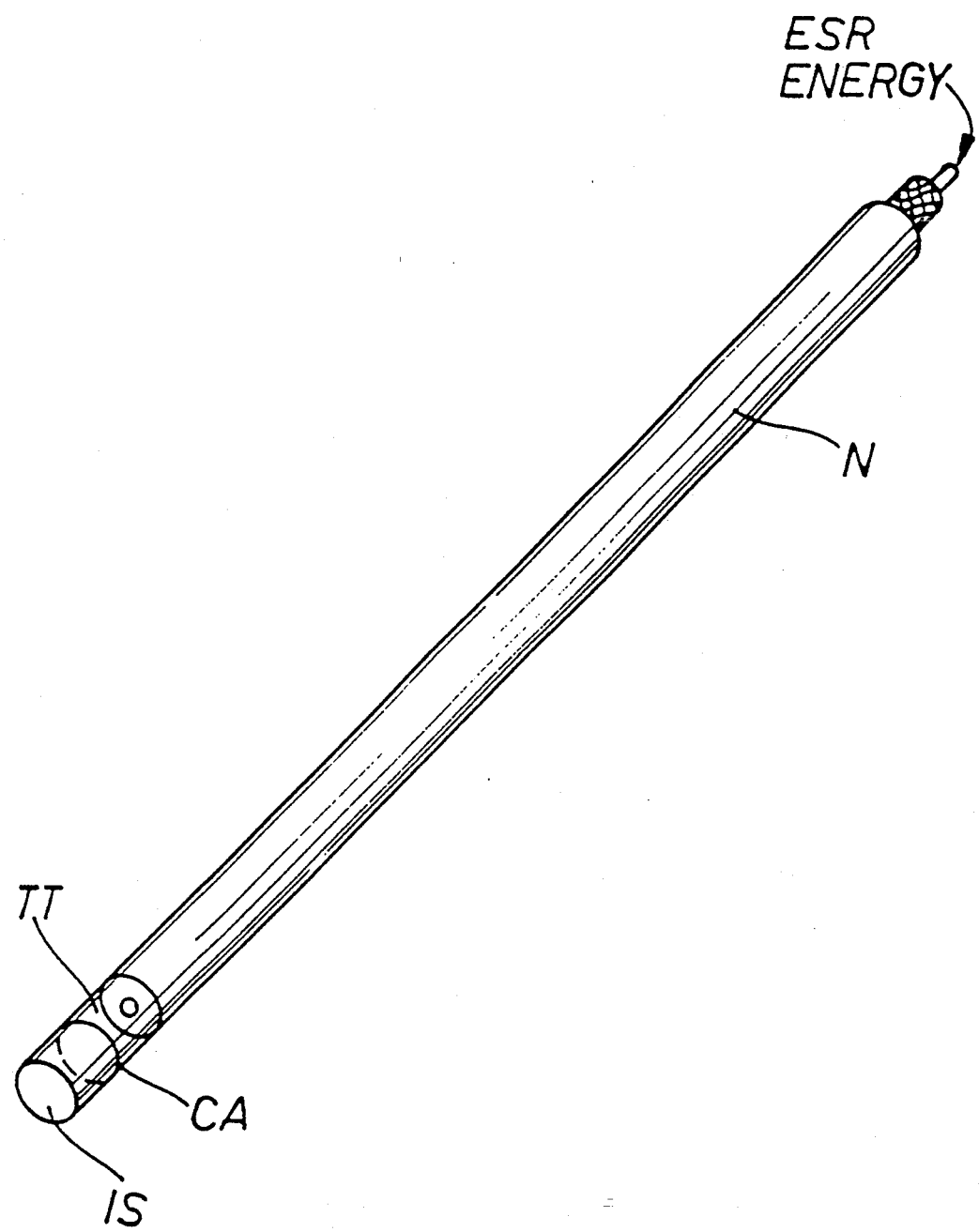

The invention will now be described in more detail with reference made to the accompanying drawings, in which FIG. shows an apparatus designed for biopsy, FIG. 2A is a perspective view of the structure of a biopsy tube instrument, FIG. 2A-1 is a cross sectional view taken along the line A—A of FIG. 2A, FIG. 2B is a perspective view of the structure of another embodiment of a biopsy tube instrument, FIG. 2B-1 is a cross sectional view taken along the line A—A of FIG. 2B, FIGS. 3A, 3B, and 3C show methods of subjecting the operative area to the action of an activating agent, FIG. 4 shows the pulse sequence of a suitable imaging method for imaging the operative location, and FIG. 5 shows the structure of a radioactive charge intended for radiation therapy.

In FIG. 1, a patient P, or some other object to be examined, is placed in polarizing magnetic field $B_o$ which is produced by a magnet M and current source MC, the action of which creates nuclear magnetization and magnetization produced by electron spins in the object. The object P is further surrounded by gradient coils GC, the strength of gradient fields produced thereby being controlled by an NMR spectrometer NMRS through the intermediary of gradient current sources G. The spectrometer NMRS also controls a radiofrequency emitter ESRE producing the energy (saturation energy) which saturates the electron spin system of materials located close to a desired part of an operative instrument, for example, biopsy needle BN. Spectrometer NMRS includes radio-frequency components necessary for procedures required to produce an NMR signal and to receive an NMR signal at antenna means A as well as for storing and processing the signal. The resulting final image is shown on a display D.

Magnet M may be a resistive, permanent or superconductive magnet, or even the earth's magnetic field can sometimes be used. Gradient coils GC in socalled rotating frame zeugmatography, produce some of the gradients in an NMR frequency excitation field.

FIGS. 2A through 2B-1 show more detailed views of the structure of a biopsy tube which can be completely coaxial as shown in FIG. 2A or partially coaxial as shown in FIG. 2B.

In FIG. 3A, an activating agent EC is injected through the cannula of an operative instrument BN into the operating area.

In FIG. 3B, an activating agent EC is bound to the surface of an operative instrument BN.

In FIG. 3C, an activating agent EC is in a separate capsule CA having semi-permeable walls so that the water molecules in the operating area are allowed a free access for interaction with the activating agent. Or the activating agent is contained, together with an NMR signal emitting material, in sealed capsule at which no such interaction takes place.

FIG. 4 illustrates an imaging method based on the 3-dimensional Fourier imaging technique for recording the position of an operative instrument by means of magnetic imaging in a manner that the first step comprises the saturation of the electron spin system of an operating area by means of the ESR frequency electromagnetic energy conducted through operative instrument BN, the second step comprises the excitation of the nuclear spin system of an operating area with the NMR frequency electromagnetic radiation, the third step comprises the phase coding of the nuclear spin system by means of z- and y- directed gradient pulses the instant of which is marked on axes $G_z$ and $G_y$, the fourth step comprises the pick-up of an NMR signal SE while the x-directed gradient is coupled and the coupling instant of this gradient is marked on axis $G_x$, the sequence being repeated a number times required by phase codings and necessary averagings and the resulting cluster of signals is reconstructed to produce a final magnetic resonance image.

FIG. 5 illustrates a capsule CA intended for radiation therapy, containing a radioactive substance (e.g. Ir-192) IS. A space TT is provided for a mixture of an activating agent EC and an NMR signal emitting agent (e.g. water). A capsule carrying needle N is provided with a coaxial conductor for carrying the ESR frequency electromagnetic energy to the proximity of space TT to saturate the electron spin system of a material contained in space TT so as to produce an activated NMR signal from the material in space TT when applying the magnetic resonance imaging method described e.g. in connection with FIG. 4.

The advantages gained by the invention in localizing an operative instrument will be obvious when comparing a signal obtained e.g. from a sample of water by means of normal MRI and DNP with a signal obtained by means of activated MRI. The activated signal may be several hundred times more powerful than a signal attainable without activation. In other words, if activation causes an amplification by 200 times, a sample of 1 mm$^3$ emits a signal which is equal to that of a sample of 200 mm$^3$. The reduction obtainable in imaging time is even more dramatic: an activated sample can be localized at the same signal-to-noise ratio 40 000 times quicker than a non-activated sample.

The sample material can be selected (e.g. silicone compounds or lipids, e g. cooking oil) in a manner that, due to chemical shift, the resonance frequency of its protons is other than e.g. that of water, whereby a sample can be accurately distinguished from a surrounding material, e.g. a biological tissue, by applying chemical shift imaging methods.

It is possible to use as an activating agent or relaxant e.g. nitrogen radicals or paramagnetic ions. In addition to the above-cited references, these have been studied e.g. in reference: Bates RD, Polarization of Solvent Nuclei by Nitroxide Spin Labels at Low Magnetic Fields, J. Magn. Reson., Vol. 48, pp. 111-124, 1982.

Technology intended for the production of ESR frequency electromagnetic energy and for carrying it to an operating area has been described e.g. in reference: Field et al, Physics and technology of hyperthermia, Martinus Nijhof Publishers, Dordrecht, the Netherlands, 1987. When conducting the saturation energy via other parts of an operative instrument to an active area, the absorption of tissues or some other medium has no effect and power demand is low. Thus, even at high ESR frequencies, there will be no thermal damages.

An operative instrument and its localizing technology can be used in connection with a stereotactic frame disclosed in U.S. patent application Ser. No. 07/738,834, filed Aug. 1, 1991.

A sample contained in the operative instrument can also be used for the observation of the degree of oxidation, temperature or a like parameter of the materials in an operating area. These physical parameters have an effect on the relaxation times of nuclei and the degree of activation obtainable by DNP. The effect of environmental conditions on a sample can be produced e.g. by encapsulating a sample in a semi-permeable membrane or by binding the activating agent to the surface of an operative instrument.

The invention is not limited to the above-described embodiments but also other embodiments are conceivable. The target nucleus can of course be any nucleus suitable for NMR tests, such as the nuclei of the NMR active isotopes of hydrogen, phosphorus, carbon, fluorine and nitrogen. Aside from medical applications, the method can be applied to the examination of animals, foodstuffs and solid objects.

I claim:

1. An operative instrument insertable in an object subjected to NMR examination for providing a localized area having improved visibility properties in an MR image of the object obtained from the examination, the examination being carried out in a magnetic field created externally of said object, said instrument comprising:

an instrument body which is sufficiently small in size, relative to said object, that the instrument body can be inserted into the object so that the object surrounds the instrument;

means coupled to said instrument body for supplying a paramagnetic relaxant to a localized area within said object and contiguous to said body instrument for interaction with NMR active nuclei capable of emitting an NMR signal and proximate to said relaxant, said paramagnetic relaxant having an electron spin system generating net magnetization in the external magnetic field; and means for supplying electron spin resonance energy via the instrument body for said relaxant to saturate its electron spin system, thereby to amplify, by dynamic nuclear polarization, the NMR signal obtained from the nuclei during the NMR examination so that said area will have improved visibility properties in an MR image.

2. An operative instrument as set forth in claim 1 wherein said means for supplying a paramagnetic relaxant comprises a closed, integral portion of said instrument body containing the relaxant.

3. An operative instrument as set forth in claim 2 wherein said instrument body portion is exposed to the exterior of said instrument body.

4. An operative instrument as set forth in claim 2 wherein said instrument body portion is covered by a semi-permeable membrane.

5. An operative instrument as set forth in claim 2 wherein said instrument body portion includes said relaxant and a substance containing said NMR active nuclei.

6. An operative instrument as set forth in claim 5 wherein said object is formed of materials having a defined NMR frequency and wherein said substance included in said instrument body portion has NMR properties which provide an NMR frequency differing, due to chemical shift, from the NMR frequency of said object.

7. An operative instrument as set forth in claim 1 wherein said means for supplying a paramagnetic relaxant comprises has means for discharging said relaxant into said localized area.

8. An operative instrument as set forth in claim 1 wherein said means for supplying electron spin resonance energy to said relaxant passes through said instrument body.

9. An operative instrument as set forth in claim 1 wherein the relaxant is bound to the surface of said instrument body.

10. An operative instrument as set forth in claim 1 wherein means for carrying out a therapeutic treatment is provided in said instrument body.

* * * * *

UNITED STATES PATENT AND TRADEMARK OFFICE
CERTIFICATE OF CORRECTION

PATENT NO. : 5,211,166
DATED : May 18, 1993
INVENTOR(S) : Raimo Sepponen

It is certified that error appears in the above-identified patent and that said Letters Patent is hereby corrected as shown below:

CLAIM 7, Col. 6, Line 53, delete "has"

Signed and Sealed this

Twenty-fifth Day of January, 1994

Attest:

BRUCE LEHMAN

Attesting Officer

Commissioner of Patents and Trademarks